United States Patent [19]

Johnson

[11] Patent Number: 4,547,608

[45] Date of Patent: Oct. 15, 1985

[54] METHANE CONVERSION USING A SILICA/MAGNESIA SUPPORT

[75] Inventor: Marvin F. L. Johnson, Homewood, Ill.

[73] Assignee: Atlantic Richfield Company, Philadelphia, Pa.

[21] Appl. No.: 600,924

[22] Filed: Apr. 16, 1984

[51] Int. Cl.$^4$ ............................................... C07C 2/00
[52] U.S. Cl. .................................... 585/500; 585/400; 585/417; 585/541; 585/654; 585/658; 585/700; 585/943
[58] Field of Search ............... 585/415, 417, 418, 500, 585/541, 654, 656, 658, 661, 943, 700

[56] References Cited

U.S. PATENT DOCUMENTS 4,205,194  5/1980  Mitchell et al. ...................... 585/500
4,239,658 12/1980  Mitchell et al. ...................... 585/500
4,443,645  4/1984  Jones et al. ......................... 585/500
4,443,648  4/1984  Jones et al. ......................... 585/500

OTHER PUBLICATIONS

Keller, G. E., "Synthesis of Ethylene via Oxidative Coupling of Methane", J. of Catalysis, 73, 9–19, (1982).
Fang, Treliant and Yeh, Chuin-Tih, "Catalytic Pyrolysis of Methane", J. of Chinese Chemical Society, 29, 265–273, (1981).

*Primary Examiner*—William R. Dixon, Jr.
*Assistant Examiner*—Cynthia A. Prezlock
*Attorney, Agent, or Firm*—Donald L. Traut

[57] ABSTRACT

An improved method for converting methane to higher hydrocarbon products by contacting a gas comprising methane with a contact agent at a selected temperature, the agent comprising a reducible metal oxide, a support of at least two oxides, and an alkali metal.

11 Claims, No Drawings

METHANE CONVERSION USING A SILICA/MAGNESIA SUPPORT

BACKGROUND OF THE INVENTION

1. Field of the Invention

This invention relates to the synthesis of hydrocarbons from a methane source. A particular application of this invention is a method for converting natural gas to more readily transportable material using a methane conversion catalyst formed using a reducible metal oxide, a support of oxides of at least two metals, and an alkali metal.

2. Description of the Pertinent Art

A major source of methane is natural gas. Other sources of methane have been considered for fuel supply (e.g., the methane present in coal deposits or formed during mining operations). Relatively small amounts of methane are also produced in various petroleum processes.

The composition of natural gas at the wellhead varies, but the major hydrocarbon present is methane. For example, the methane content of natural gas may vary within the range of about 40 to about 95 volume percent. Other constituents of natural gas include ethane, propane, butane, pentane (and heavier hydrocarbons), hydrogen sulfide, carbon dioxide, helium, and nitrogen.

Natural gas is classified as dry or wet, depending upon the amount of condensable hydrocarbons contained in it. Condensable hydrocarbons generally comprise $C_3+$ hydrocarbons, although some ethane may be included. Gas conditioning is required to alter the composition of wellhead gas; processing facilities usually being located in or near the production fields. Conventional processing of wellhead natural gas yields processed natural gas containing at least a major amount of methane.

Large-scale use of natural gas often requires a sophisticated and extensive pipeline system. Liquefaction has also been employed as a transportation means, but processes for liquefying, transporting and revaporizing natural gas are complex, energy intensive and require extensive safety precautions. Transport of natural gas has been a continuing problem in the exploitation of natural gas resources. It would be extremely valuable to be able to convert methane (e.g., natural gas) to more readily transportable products. Moreover, direct conversion to olefins such as ethylene or propylene would be extremely valuable to the chemical industry.

Recently, it has been discovered that methane may be converted to higher hydrocarbons by a process which comprises contacting methane with an oxidative synthesizing agent at synthesizing conditions (e.g., at a temperature selected within the range of about 500° to about 1000° C.). An oxidative synthesizing agent is a composition having as a principal component at least one oxide of at least one metal, which composition produces higher $C_2+$ hydrocarbon products, water and a composition comprising a reduced metal oxide when contacted with methane at synthesizing conditions. Reducible oxides of several metals have been identified which are capable of converting methane to higher hydrocarbons. In particular, oxides of manganese, tin, indium, germanium, lead, antimony and bismuth are most useful.

The reaction products of such processes are mainly ethylene, ethane, other light hydrocarbons, carbon oxides, coke and water. It would be beneficial to these oxidative synthesis processes to reduce production of carbon oxides and coke.

Accordingly, an object of this invention is to provide an improved process for converting methane to higher hydrocarbons. A further object of this invention is an improved oxidative synthesizing agent——one capable of converting methane with reduced byproduct selectivities.

Other aspects, objects and the several advantages of this invention will become apparent to those skilled in the art upon reading this Specification and the appended claims.

SUMMARY OF THE INVENTION

An improved hydrocarbon conversion process has been discovered which comprises contacting hydrocarbons, preferably a gas comprising methane, with a contact agent at conditions to convert the hydrocarbons, preferably at a temperature selected within the range of about 500° to about 1000° C., which agent comprises:

(a) at least one reducible oxide of at least one metal, which oxide is reduced and produces higher hydrocarbon products and water when contacted with methane at the selected temperature;

(b) a support comprising first and second oxides, preferably solid oxides, the first oxide comprising alkaline earth oxides, the second oxide selected from a group consisting of silica, alumina, and mixtures thereof, and the mole ratio of the first oxide to the second oxide being less than about 1:1; and (c) an alkali metal.

DETAILED DESCRIPTION OF THE INVENTION

The contact agent of this invention is a composition comprising at least one reducible oxide of at least one metal and a support. The reducible oxide produces higher hydrocarbon products, water and a reduced metal oxide when contacted with methane at a temperature selected within the range of about 500 to about 1000° C. The term "reducible" is used to identify those oxides of metals which are reduced by the methane contact. The term "oxide(s) of metal(s)" includes: (1) one or more metal oxides (i.e., compounds described by the general formula $M_xO_y$ wherein M is a metal, O is oxygen, and the subscripts x and y designate the relative atomic proportions of metal and oxide in the composition); and/or (2) one or more oxygen-containing metal compounds; provided that such oxides and compounds have the capability of performing to produce higher hydrocarbon products as set forth herein.

The preferred agents comprise reducible oxides of metals selected from the group consisting of manganese, tin, indium, germanium, antimony, lead, bismuth, and mixtures thereof. The particularly preferred agents comprise reducible oxides of manganese and mixtures of reducible oxides of manganese with other agents.

The support comprises at least two oxides. Preferably, at least one of the oxides is an alkaline earth oxide and the second oxide is selected from a group comprising silica, alumina, and mixtures thereof. More preferably, the first oxide comprises magnesia and the second oxide comprises silica.

The preferred mole ratio of the first oxide to the second oxide is about 1:9 or greater, and more preferably is in the range of about 1:2 to about 1:3. Particularly good results are obtained when this ratio is about 3:7.

The preferred contact agent of this invention contains, in addition to the foregoing elements, at least one alkali metal. Sodium and/or compounds thereof are a particularly preferred alkali metal component. Except as noted elsewhere herein, the atomic ratio in which these materials are combined to form the contact agent is not narrowly critical. However, the preferred atomic ratio of the reducible oxide component (expressed as the metal, e.g., Mn) to the alkali metal component (expressed as the metal, e.g., Na) is within the range of about 0.1:1 to about 100:1, more preferably within the range of about 0.3:1 to about 10:1. The preferred mole ratio of silica or alumina to alkali metal is about 50:1 to about 1:1, and more preferably about 0.5:1 to about 10:1. Most preferably, the ratio is about 1:1 to about 3:1.

The alkali metal component may be added to the support before or during precipitation, coprecipitation, or impregnation of the reducible oxide and the support.

The support or agent may be contacted with a suitable alkali metal component which should not interfere with the support function, the reducible oxide function, or the process for combining the support with the reducible oxide. Preferably, the alkali metal component is a basic composition of the alkali metal. More preferably, the alkali metal component is selected from a group consisting of sodium hydroxide, sodium acetate, lithium hydroxide, lithium acetate, and mixtures thereof.

The contact agent can be prepared by any suitable method. Conventional methods such as precipitation, coprecipitation, impregnation, granulation, and spray drying can be used.

One suitable method of preparation of the contact agent includes the following steps.

An aqueous slurry of magnesia and silica gel is prepared and mixed with a solution of reducible oxides.

Suitable metal compounds useful for impregnation include the acetates, acetylacetonates, oxides, carbides, carbonates, hydroxides, formates, oxalates, nitrates, phosphates, sulfates, sulfides, tartrates, fluorides, chlorides, bromides or iodides.

After impregnation, the resulting composite is dried in an oven to remove solvent and the dried solid is prepared for use by calcining at elevated temperatures in an oxygen-containing gas (e.g., air) prior to use in the process of this invention. Particular calcination temperatures will vary, depending upon the particular metal compound or compounds employed. Preferably, the air temperature is selected within the range of about 300 to about 1200° C.

In addition to methane, the preferred feedstock employed in the method of this invention may contain other hydrocarbon or non-hydrocarbon components, although the methane content should typically be within the range of about 40 to about 100 volume percent, preferably about 80 to about 100 volume percent, more preferably about 90 to about 100 volume percent.

Operating temperature for contacting the methane with the contact agent are preferably selected within the range of about 500° to about 1000° C.; the particular temperature selected depending upon the particular reducible metal oxide(s) employed in the contact agent. For example, reducible oxides of certain metals may require operating temperatures below the upper part of the recited range to minimize sublimation or volatilization of the metals (or compounds thereof) during methane contact. Examples include reducible oxides of indium, germanium and bismuth (operating temperatures will preferably not exceed about 850° C.).

Operating pressure for the methane contacting step are not critical to the presently claimed invention. However, both general system pressure and partial pressure of methane have been found to affect overall results. Preferred operating pressures are within the range of about 1 to about 30 atmospheres.

Contacting methane and a reducible metal oxide to form higher hydrocarbons from methane also produces reduced metal oxides and water. The exact nature of the reduced metal oxides is unknown, and so is referred to herein as "reduced metal oxides". Regeneration of a reducible metal oxide is readily accomplished by contacting such reduced materials with oxygen (e.g., an oxygen-containing gas such as air) at elevated temperatures, preferably at a temperature selected within the range of about 300 to about 1200° C.; the particular temperature selected depending on the metal(s) included in the contact agent.

In carrying out the present process, a single reactor apparatus containing a fixed bed of solids may be used with intermittent or pulsed flow of a first gas comprising methane followed by intermittent or pulsed flow of a second gas comprising oxygen (e.g., oxygen, oxygen diluted with an inert gas, or air, preferably air). The methane contacting step and the oxygen contacting step may also be performed in physically separate zones with solids recirculating between the two zones.

Thus, a suitable method for synthesizing hydrocarbons from a methane source comprises: (a) contacting a gas comprising methane and particles comprising a contact agent to form higher hydrocarbon products, water and reduced metal oxide; (b) removing particles comprising reduced metal oxide from the first zone and contacting the reduced particles in a second zone with an oxygen-containing gas to form particles comprising a contact agent; and (c) returning the particles produced in the second zone to the first zone. The steps are preferably repeated at least periodically, and more preferably the steps are continuous. In the more preferred embodiment, solids are continuously circulated between at least one methane contact zone and at least one oxygen contact zone.

Particles comprising a reducible metal oxide which are contacted with methane may be maintained as fluidized, ebullating, or entrained beds of solids. Preferably, methane is contacted with a fluidized bed of solids.

Similarly, particles comprising reduced metal oxide which are contacted with oxygen may be maintained as fluidized, ebullating, or entrained beds of solids. Preferably, oxygen is contacted with a fluidized bed of solids.

In the more preferred embodiment of the present invention, methane feedstock and particles comprising a contact agent are continuously introduced into a methane contact zone maintained at synthesizing conditions. Synthesizing conditions include the temperatures and pressures described above. Gaseous reaction products from the methane contact zone (separated from entrained solids) are further processed (e.g., passed through a fractionating system wherein the desired hydrocarbon products are separated from unconverted methane and combustion products.) Unconverted methane may be recovered and recycled to the methane contact zone.

Particles comprising reduced metal oxide are contacted with oxygen in an oxygen contact zone for a time sufficient to oxidize at least a portion of the reduced metal oxide to produce a reducible metal oxide and to remove (i.e., combust) at least a portion of any carbonaceous deposit which may form on the particles in the methane contact zone. The conditions of the oxygen contact zone will preferably include a temperature selected within the range of about 300° to 1200° C., pressures of up to about 30 atmospheres, and average particle contact time within the range of about 1 to about 120 minutes. Sufficient oxygen is preferably provided to oxidize all reduced metal oxide to produce a reducible metal oxide and to completely combust any carbonaceous deposit material deposited on the particles. At least a portion of the particles comprising the contact agent which are produced in the oxygen contact zone are returned to the methane contact zone.

The rate of solids withdrawal from the methane contact zone is desirably balanced with the rate of solids passing from the oxygen contact zone to the methane contact zone so as to maintain a substantially constant inventory of particles in the methane contact zone, thereby enabling steady-state operation of the synthesizing system.

The present invention is further illustrated by reference to the following Examples.

EXAMPLE I 27.6 grams of $NaMnO_4$—$3H_2O$ (Pfaltz and Bauer SO-5560) was dissolved in 525 ml. of water. The solution and 144 grams of magnesia (Catalyst Resources, Inc. MgO-700) were slurried for 1 hour at 150° F. The solid material was dried for 2 hours at 230° C., crushed and then screened through a 60-mesh sieve. The powder was then calcined for 16 hours at 800° C.

EXAMPLE II 137 grams of spray-dried silica-magnesia (Grace Davison SM-30) was calcined for 16 hours at 550° C. 27.6 grams of $NaMnO_4$—$3H_2O$ was dissolved in 135 ml. of water—the volume required for pore filling the calcined silica/magnesia. The calcined silica/magnesia was impregnated with the permanganate solution. The material was dried for 2 hours at 230° C., crushed and then screened through a 60-mesh sieve. The powder was then calcined for 16 hours at 800° C.

Methane contact runs were made at about atmospheric pressure in quartz tube reactors (12 mm. inside diameter) partially packed with 10 ml. of contact solid. The reactors were brought up to temperature under a flow of heated nitrogen which was switched to methane at the start of the run. Unless otherwise indicated, all methane contact runs described in the Examples had a duration of two minutes. At the end of each methane contact run, the reactor was flushed with nitrogen and the solids were regenerated under a flow of heated air (usually at 800° C. for 30 minutes). The reactor was then again flushed with nitrogen and the cycle repeated. Most of the results reported below are based on the cumulative samples collected after the contact solids were "equilibrated"; i.e., after the aberrant characteristics of the fresh contact solid had dissipated. This allows more meaningful comparison between the contact solid within the scope of the present invention and other contact solids. Three to six cycles of methane contact and regeneration are generally sufficient to equilibrate the catalyst.

Space velocities are reported as gas hourly space velocities (hr.$^{-1}$) (GHSV) and were 600 GHSV for the Examples. The results are shown in Table 1 below.

TABLE 1

| Ex. No. | Test No. | Atomic Ratio vs. Na | | | | % Conv. | % Selec. | % $C_2$ Yield |
|---|---|---|---|---|---|---|---|---|
| | | Na | Mn | Mg | Si | | | |
| I | 5523-06 | 1 | 1 | 25.4 | — | 14.2 | 11.2 | 1.6 |
| II | 5525-16 | 1 | 1 | 2.0 | 11.8 | 1.4 | 66.7 | 0.9 |

What is claimed is:

1. In an method for converting a gas comprising methane to higher hydrocarbons which comprises contacting said gas with a contact agent at conditions to convert said gas, said contact agent comprising:
   (a) at least one metal, the oxide of which is reduced and produces higher hydrocarbons and water when contacted with methane at a selected temperature in the range of about 500° to about 1000° C.; and
   (b) a support comprising at least two oxides, and
   (c) an alkali metal, the improvement which comprises employing said contact agent wherein said support further comprises a first and a second oxide, said first oxide 2. The method of claim 1 wherein said at least one metal is selected from a group consisting of manganese, tin, indium, germanium, antimony, lead, bismuth, and mixtures thereof.

3. The method of claim 1 wherein said alkali metal is selected from a group consisting of lithium, sodium, potassium, rubidium, cesium, and mixtures thereof.

4. The method of claim 3 wherein said alkali metal is selected from a group consisting of sodium, sodium compounds, and mixtures thereof.

5. The method of claim 1 wherein said support comprises magnesia.

6. The method of claim 1 wherein said support comprises silica.

7. The method of claim 6 wherein said support comprises magnesia and silica.

8. The method of claim 1 wherein said support comprises a mole ratio of said first oxide to said second oxide greater than about 1:9.

9. The method of claim 8 wherein the mole ratio of said first oxide to said second oxide is about 1:2 to about 1:3.

10. The method of claim 9 wherein said first oxide comprises magnesia, said second oxide comprises silica, and the ratio of said magnesia to said silica is about 3:7.

11. The method of claim 1 wherein said mole ratio of said second metal oxide to said alkali metal is about 0.5:1 to about 10:1.

* * * * *

UNITED STATES PATENT AND TRADEMARK OFFICE
CERTIFICATE OF CORRECTION

PATENT NO. : 4,547,608

DATED : October 15, 1985

INVENTOR(S) : Marvin F. L. Johnson

It is certified that error appears in the above-identified patent and that said Letters Patent is hereby corrected as shown below:

Claim 1, Column 6, Line 17

After "In an" add -- improved --.

Claim 1, Column 6, Line 30

Add after "first oxide"

-- comprising alkaline earth oxides, said second oxide selected from a group consisting of silica, alumina, and mixtures thereof, and the mole ratio of said first oxide to said second oxide being less than about 1:1. --

Signed and Sealed this

Seventeenth Day of June 1986

[SEAL]

Attest:

DONALD J. QUIGG

Attesting Officer

Commissioner of Patents and Trademarks